United States Patent [19]

Gubelmann et al.

[11] Patent Number: 5,118,651

[45] Date of Patent: Jun. 2, 1992

[54] CHEMICAL COMPOUND CONTAINING ALKALI METALS OR ALKALINE EARTH METALS, CATALYST CONTAINING THE COMPOUND AND PROCESS FOR THE PRODUCTION OF THE CATALYST

[75] Inventors: Michel Gubelmann, Lyon; Philippe-Jean Tirel, Oulins; Claude Doussain, Saint-Fons; Helene Pernot, Paris; Laurent Gilbert, Lyon; Jean-Michel Popa, Drancy, all of France

[73] Assignee: Rhone-Poulenc Chimie, Cedex, France

[21] Appl. No.: 648,621

[22] Filed: Feb. 1, 1991

Related U.S. Application Data

[63] Continuation-in-part of Ser. No. 547,079, Jul. 5, 1990, abandoned, which is a continuation-in-part of Ser. No. 388,936, Aug. 3, 1989, Pat. No. 4,950,811.

[30] Foreign Application Priority Data

Feb. 2, 1990 [FR] France .................. 90 01264

[51] Int. Cl.⁵ .................. B01J 23/02; B01J 23/18; B01J 27/18
[52] U.S. Cl. .................. 502/202; 502/208; 502/243; 502/246; 502/249; 502/302; 502/303; 502/304; 502/340; 502/344
[58] Field of Search .................. 502/208, 202, 243, 246, 502/249, 302, 303, 304, 340, 344

[56] References Cited

U.S. PATENT DOCUMENTS

| | | | |
|---|---|---|---|
| 3,393,043 | 7/1968 | Kribbe et al. | 23/106 |
| 3,655,334 | 4/1972 | Kribbe | 23/106 |
| 3,862,964 | 1/1975 | Weisang et al. | 252/437 |
| 4,560,798 | 12/1985 | Ford et al. | 564/503 |
| 4,729,978 | 3/1988 | Sawicki | 502/174 |
| 4,761,393 | 8/1988 | Baleiko et al. | 502/208 |

FOREIGN PATENT DOCUMENTS

| | | |
|---|---|---|
| 0228898 | 7/1987 | European Pat. Off. . |
| 2192083 | 2/1974 | France . |
| 474452 | 6/1969 | Switzerland . |

Primary Examiner—W. J. Shine
Attorney, Agent, or Firm—Finnegan, Henderson, Farabow, Garrett and Dunner

[57] ABSTRACT

The invention relates to chemical compounds and their use as catalysts in the solvolysis of alkyl halides. The chemical compounds, when dry, have formula (I):

$$(EO_4M)\cdot(Imp)_p \quad (I)$$

wherein E is selected from the group consisting of phosphorus, arsenic, antimony and bismuth, and is preferably phosphorus, and M is a metal or a mixture of metals. Imp corresponds to a basic impregnating compound consisting of alkaline earth metal, or preferably alkali metal, and their mixtures in combination with a counter-anion to ensure electrical neutrality.

The coefficient p is between $10^{-2}$ and $\frac{1}{3}$.

27 Claims, No Drawings

CHEMICAL COMPOUND CONTAINING ALKALI METALS OR ALKALINE EARTH METALS, CATALYST CONTAINING THE COMPOUND AND PROCESS FOR THE PRODUCTION OF THE CATALYST

This application is a Continuation-In-Part of Ser. No. 547,079 filed Jul. 5, 1990, presently pending, which is a Continuation-In-Part of Ser. No. 07/388,936 filed Aug. 3, 1989, now U.S. Pat. No. 4,950,811. These applications are hereby incorporated by reference.

The present invention relates to new chemical compounds which can be used as catalysts for reactions such as the solvolysis of an alkyl halide, especially when the carbon carrying a halogen is in the vicinity of an attracting group or groups, such as the trifluoromethyl group.

The present invention also relates to new chemical compounds which can be used as catalysts for reactions such as dehydrohalogenation of alkyl halides.

The present invention further relates to a process for the solvolysis, preferably gas phase solvolysis, of an organic halide. For example, the invention relates to the preparation of trifluoroethanol by hydrolysis, in the gas phase, from 2,2,2-trifluoroethyl chloride.

There have been many difficulties in the conversion of 2,2,2-trifluoroethyl chloride to the corresponding alcohol by solvolysis wherein water is the solvent (hydrolysis). 2,2,2-trifluoroethyl chloride is an example of the alkyl halides for which solvolysis is ordinarily difficult.

2,2,2-trifluoroethanol (TFE) is a trifluorinated alcohol possessing very good thermal stability, which makes it suitable for a number of applications, in particular in the synthesis of fluorinated anesthetics, in pharmacology in general, and as a solvent.

The preparation of this alcohol either by hydrogenation of trifluoroacetic acid or its esters, or by hydrolysis of 2,2,2-trifluoroethyl acetate, in liquid phase in a solvent having hydroxyl groups, has been described in the prior art.

These various processes for the preparation of TFE are not research has been undertaken in order to find out if it would be possible to carry out a direct hydrolysis, in the gas phase, of 1-chloro-2,2,2-trifluoroethane.

Unpublished French application number 88/10,813 which corresponds to U.S. Ser. No. 07/388,936 by the Applicants, now U.S. Pat. No. 4,950,811, constitutes a significant advance. The process for the preparation of trifluoroethanol by hydrolysis of trifluorochloroethane, according to the French application, comprises contacting a mixture of 1-chloro-2,2,2-trifluoroethane and water with a solid catalyst comprising at least one phosphate, or hydrophosphate, or one oxide of a di- or trivalent metal, at a temperature greater than 350° C. and preferably between 400 and 500° C. Hydrolysis is a type of solvolysis wherein water is used as the solvent. The success of the hydrolysis in this application is surprising because it is known to those skilled in the art that the electro-attractive power of the $CF_3$ group of the 1-chloro-2,2,2-trifluoroethane molecule reduces, or at least renders difficult, the possibility of attacking, with a nucleophilic compound, the carbon atom which is linked to the chlorine of this molecule.

It is an object of the present invention to provide catalysts which introduce a better selectivity and good yields in the above solvolysis processes. chemical compounds which, when used as catalysts, lead to good selectivity and to good yields during reactions such as that of solvolysis, for example hydrolysis, of alkyl halide(s).

Another object of the present invention is to provide a process for the production of such chemical compounds.

Another object of the present invention is the reaction such as that of a solvolysis, for example hydrolysis, of alkyl halides using the above-mentioned catalysts.

Another objective of the present invention is to provide chemical compounds which can be used as catalysts in dehydrohalogenation reactions.

Another object of the present invention is to prepare trifluoroethanol by hydrolysis, in the gas phase, of chloro-trifluoroethane.

These objects and others which will become apparent below.

Chemical Compounds for use as Catalysts and Process of Making

Chemical compounds useful as catalysts have, when dry, the formula:

$$(EO_4M).(Imp)_p \qquad (I)$$

wherein E is selected from phosphorus, arsenic, antimony and bismuth, and is preferably phosphorus;

M is a metal or a mixture of metals such that:

$$M = \alpha M_1^+ \beta M_2^{++} + \gamma M_3^{3+} + \delta M_4^{4+}$$

with the relationship $\alpha + 2\beta + 3\gamma + 4\delta = 3$.

$M_1$ is selected from lithium, sodium, potassium, rubidium, cesium, francium and mixtures thereof, and is preferably one of the alkali metals. Preferred among the alkali metals are potassium, rubidium, cesium and mixtures thereof. More preferred are potassium, cesium and mixtures thereof.

$M_2$ is selected from the divalent transition elements, and alkaline earth metals and mixtures thereof. The transition elements can include zinc and cadmium. Preferably, $M_2$ consists predominately or totally of alkaline earth metal(s). The preferred alkaline earth metals are calcium, strontium and barium mixtures thereof and mixtures containing them.

$M_3$ is selected from the trivalent transition elements, boron, aluminum, gallium, indium, thallium, the elements having an f electron subshell and the like, and mixtures thereof. Preferably $M_3$ consists predominantly or totally of elements having a subshell f. Preferred metals containing a sub-shell f are atrium and rare earth metals, such as, lanthanum, and lanthanides, preferably lanthanum, mixtures thereof and mixtures containing them.

$M_4$ is selected from the tetravalent rare earths, titanium, hafnium and tin. $M_4$ can also be germanium or silicon.

$\alpha$ is a coefficient between 0 and 3, preferably from greater than 0.01 to 3, more preferably from greater than 0.01 to not more than 0.5, and most preferably between 0.05 and 0.2.

$\beta$ is a coefficient between 0 and 3/2 and preferably between 0 and ⅓ or 1±0.1.

$\gamma$ is a coefficient between 0 and 1, preferably from at least ⅓ to 1, and more preferably ½.

$\delta$ is a coefficient between 0 and ¾, preferably between 0 and ⅓ and more preferably between 0 and 1/6.

Imp corresponds to an impregnating compound selected from metal selected from alkaline earth metals, alkali metals and mixtures thereof, such as discussed above, and preferably, potassium, rubidium, sodium, cesium and mixtures thereof and more preferably cesium. Lithium is preferable for dehydrohalogenation. The metals are combined with a counter-anion to ensure electrical neutrality.

Imp is preferably different from impregnant $MEO_4$, especially when the impregnant is an alkaline earth metal compound. The impregnant may be described as basic because, in the majority of cases, the impregnant is a proton-acceptor, particularly after having been conditioned at a temperature close to that of the solvolysis reaction.

The initial counteranion(s), i.e. before thermal conditioning, is (are) preferably selected from halides, preferably fluoride, and mixtures containing the halides, $OH^-$ and mixtures containing $OH^-$, preferably mixtures containing predominately $OH^-$, and derivatives of the $EO_4^{3-}$ class such as phosphates and hydrogen phosphates and those which become these after pyrolysis, such as, for example, phospho- or phosphinate, and mixtures of such derivatives. Some examples of phosphates are dihydrogeno phosphate, monohydrogeno phosphate, trianionic phosphate ($PO_4^{3-}$).

Furthermore, the initial counteranion(s) can be selected from volatile or decomposable anions such as carbonate(s), nitrate, sulfate(s), carboxylates and sulfonates which can be decomposed under the conditions of the reaction, e.g. solvolysis, or thermal conditioning. The anions that are either obtained under these conditions (e.g. oxygenated anions such as $O^{-2}$ or $OH^-$, or those, such as halides, that are part of the reaction phase which are substituted to the initial anion or the oxygenated anions) or that remain unchanged provide for good catalysts.

It has been discovered that the best catalysts are those in which the impregnation is carried out on a matrix ($MEO_4$) which has a structure containing holes (pores), preferably channels. The size (diameter) of the holes is preferably between 0.2 and 0.5 nm, structure of the matrix may be of a hexagonal type, a monoclinic type or other types.

Especially when 7 is higher than $\frac{1}{2}$, preferably higher than $\frac{2}{3}$, the best catalysts for the solvolysis reactions are those whose matrix ($ME04$) is of hexagonal or monoclinic structure, preferably those whose matrix has, at least at low temperature, a hexagonal structure (that is to say with a $C_6$ symmetry axis parallel to the zeolitic channels, the system of channels being one-dimensional and not interconnected, structural defects being, of course, not taken into account). More preferably it has been shown that the best catalysts are those in which the impregnation is carried out on a matrix which has at least partially a structure of a hexagonal type. However, direct impregnation of monoclinic structures also provide good catalysts.

Finally, it is also preferable that, on heating, the hexagonal structure of the matrix should be capable of being converted into a monoclinic structure. Further that, after impregnation, the compound according to the invention should be subjected to conditions which ensure the hexagonal-monoclinic conversion.

Although this explanation should not be taken to imply any limit, it would appear that the good catalytic power observed in the case of the hexagonal structures might be correlated with the filling of the channels, or holes, of the hexagonal structure with the alkali-metal or alkaline-earth metal material and that this is so even though no detectable trace remains when the hexagonal structure is investigated by the usual means.

The selectivity of the reaction is also dependent on the alkali-metal or alkaline-earth metal material. The higher the ranking of the period to which it belongs, the more the solvolysis reaction is promoted; on the other hand, the lower the ranking, the more the dehydrohalogenation reaction is promoted.

In general, the compounds according to the invention which give mediocre selectivities in solvolysis give results of opposite quality in dehydrohalogenation. In other words, everything takes place as if the substrates had the choice between the two main possible routes (solvolysis or dehydrohalogenation) and as if by choosing the catalysts (according to the above directing principles) it was possible to promote either of the reactions.

The coefficient p represents the ratio between the impregnating compound expressed in gram equivalent and the impregnated compound ($EO_4M$) expressed in mole. The coefficient p is between $10^{-2}$ and $\frac{1}{3}$, preferably between 0.05 and $\frac{1}{4}$ and more preferably between $\frac{1}{2} \times 10^{-1}$ and 1/5.

Moreover, $\alpha + p$ is less than or equal to 3.3 and greater than or equal to $10^{-2}$, preferably between 0.05 and 1 and more preferably between 0.05 and $\frac{1}{2}$.

These compounds can be produced by impregnating a compound to the formula:

$$EO_4M \qquad (II)$$

wherein M has the same definition as M defined above, with a solution or a suspension of Imp in a volatile solvent, preferably water. The results are better if Imp is soluble and the compound $EO_4M$ is freshly produced. Processes for the production of $EO_4M$ are known in the art. See, for example, Pascal P., Nouveau Traite De Chimie Minerale, Vol. X: 821-823 (1956), and Gmelins Handbuch. Der Anorganischen Chemie (8th ed.), Vol. 16 (C): 202-206 (1965) which are specifically incorporated by reference herein.

The process for the synthesis of a compound of formula I comprises, a) synthesizing the compound $EO_4M$; then, preferably without separating $EO_4M$ from the reaction mixture, b) introducing an impregnating compound into the reaction mixture;

c) separating any residual liquid from the reaction solid; and d) drying and calcining the solid, if appropriate, at a temperature greater than 100° C. to obtain the catalyst ($EO_4M$) $(Imp)p$.

General techniques for the production of phosphates are discussed in Pascal P., Nouveau Traite De Chimie Minerale, Vol. X: 821-823 (1956), and Gmelins Handbuch Der Anorganischen Chemie (8th ed.), Vol. 16 (C): 202-206 (1965), wherein two main routes for access to the phosphates can be distinguished. One technique is the precipitation of a soluble salt of the metal (chloride, nitrate) by ammonium hydrogen phosphate and a finishing treatment with ammonia followed by completion of the neutralization. Another technique is the reaction of the metal oxide with phosphoric acid under hot conditions and a finishing treatment with an alkali metal hydroxide.

Within the framework of the present invention, the second procedure enables the cation of the hydroxide employed in the finishing phase to be introduced and impregnated into the final product (I).

According to the present invention, these chemical compounds, $(EO_4M)(Imp)_p$, can be used as catalysts for the solvolysis of a halogenated compound. Further, these catalysts may be used for dehydrohalogenation. The catalysts according to the present invention can be catalytic bodies the surfaces of which will be formed at least in part by a chemical compound (I) according to produced entirely of chemical compounds (I).

It has been found, surprisingly, that the first few minutes and up to ten minutes generally give less than optimum results with regard to the selectivity of the solvolysis. It is generally only after the catalyst has been modified by the passage of the reactants for a period which can vary from ten minutes up to 2 hours under the solvolysis conditions that the catalyst will play its role of selective catalyst to the full.

The catalyst or catalytic body can be of any shape known per se for solid catalysts which can be used in the gas phase.

The remainder of a catalytic body, that is the part which mixture, can be of any material or materials provided that it is inert under the conditions of use. For reasons of ease of production, the remainder can be made of compounds selected from phosphates, hydrogen phosphates and mixture thereof. The specific surface-area of the pure catalysts or catalytic body, ranges from at least 1 $m^2/g$, preferably at least 10 $m^2/g$ and most preferably between 10 and 100 $m^2/g$.

Solvolysis Process using the Catalysts

The present invention also relates to a solvolysis process using the above catalysts. This process relates more particularly to the alkyl halides in which the alkyl term corresponds to the definition given in the chemical dictionary "Presse Scientifique, Paris VI, 1959" (Ed. Duval). As described below, the alkyl halide is reacted with a solvent-reactant.

Preferably, the alkyl radical corresponding to the alkyl halide has one or more of the following characteristics:

it is electron-attracting,
it does not carry hydrogen on the carbon or carbons in the position vicinal to that which carries the leaving group Y,
it carries halogens or equivalent groups, for example $CF_3$, on said vicinal carbon or carbons,
it is stable under the operating conditions.

The alkyl halide preferably has the formula:

$$R-CX_2-CH_2Y \qquad (III)$$

R in formula (III) preferably represents a fluorinated or perfluorinated alkyl or a halogen. The R group is such that the boiling point is at a pressure of $10^4$ Pa, preferably at a pressure of $10^5$ Pa, at most equal to the reaction temperature. Preferably R contains at most 50 carbon atoms, preferably at most 25 carbon atoms and more preferably at most 10 carbon atoms.

In the same formula (III), each X preferably represents a fluorine atom. The remaining halogen, Y, preferably represents chlorine for economic reasons, or fluorine, which is very selective, although not very efficient, for the solvolysis The solvolysis reaction preferably takes place in the gas phase. The solvolysis temperature is preferably between about 200 and 800° C., and more preferably between about 400 and 600° C.

Although carrying out the reaction at pressures of atmospheric pressure or lower can be envisaged, it has been found, surprisingly, that it is preferably worthwhile to operate at a pressure higher than normal pressure, i.e., between about 1 and 100 atmospheres ($10^5$ to $10^7$ Pa) and more preferably from about 1 to 20 atmospheres ($10^5$ to $2 \times 10^8$ Pa).

The molar ratio between solvent-reactant and substrate (alkyl halide) is between 1:1 and 100:1 and preferably between 2:1 and 10:1.

To obtain good results, the catalytic flow rate, expressed in grams of substrate per gram of catalyst (per hour), is between 0.05:1 and 10:1 $h^{-1}$ and preferably between 0.5:1 and 5:1 $h^{-1}$.

The apparent density of the catalyst is preferably between 0.3 and 2 and more preferably between 0.8 and 1.5.

A carrier gas is optional and is usually a gas, or a mixture of gases, which is not reactive under the operating conditions (for example $N_2$, air, $H_2$, He and the rare gases; $N_2$ and $H_2$ are preferred). The ratio by volume with the substrate varies from $10^{-2}:1$ to 50:1, preferably 0.5:1 to 30:1 and more preferably 0.5:1 to 10:.

The solvent-reactant preferably has a pressure at the temperature of the reaction of at least $10^5$ Pa, preferably $10^6$ Pa. The solvent-reactant used for the solvolysis is preferably a protic polar nucleophilic solvent which does not give rise to a significant parasitic reaction under the operating conditions.

Solvent-reactants giving the best results include primary or secondary amines, including anilines, and alcohols, including phenols. Water also gives particularly good results.

When a dehydrogenation reaction is desired, it is preferable to reduce the solvent or use no solvent at all. If a solvent is used, the solvent is preferably water.

The following non-limiting examples illustrate the invention..

EXAMPLES

Examples C1-C6

Preparation of catalysts—General operating method using doped $LaPO_4$

Metal oxide $La_2O_3$ (0.5 mole) was added in the course of 30 minutes to an 86% solution of $H_3PO_4$ (1 mole) in distilled water (300 cc) at a temperature of 90° C. and with good stirring. An aqueous solution of an alkali metal or alkaline earth metal hydroxide (0.2 mole) was added until the mixture is neutral was recovered by filtering off, washed with distilled water, dried at 100° under 200 torr for 16 hours and calcined at 500° C. for 3 hours under air.

The data provided by elemental analysis are collated in Table 1.

TABLE 1

| | Synthesis of "$LaPO_4$, M" | | | | | |
|---|---|---|---|---|---|---|
| | "Dopant" | Elemental analyses (%) | | | Atomic ratio | |
| Ex. | M | La | P | M | M/La* | La/M |
| C1 | Li | 54.02 | 11.5 | 0.34 | 0.13 | 7.7 |
| C2 | Na | 53.9 | 11.3 | 0.9 | 0.10 | 10 |
| C3 | K | 53.95 | 11.3 | 1.25 | 0.08 | 12.5 |
| C4 | Cs | 55.0 | 11.4 | 3.5 | 0.06–0.07 | 15.4 |
| C5 | Sr | 53.6 | 12.6 | 4.0 | 0.12 | 8.3 |

TABLE 1-continued

| | "Dopant" | Synthesis of "LaPO4, M" Elemental analyses (%) | | | Atomic ratio | |
|---|---|---|---|---|---|---|
| Ex. | M | La | P | M | M/La* | La/M |
| C6 | Ba | 51.1 | 11.7 | 5.6 | 0.12 | 8.3 |

*Here the ratio M/La corresponds to $\frac{a-p}{1-\frac{a}{3}}$ which is approximately $a \div p$

Procedure for solvolysis

Generally, the reactor was heated for half an hour at the desired reaction temperature, then the gaseous reactant mixture (solvent and 1-chloro-2,2,2-trifluoroethane) was circulated in the tube (entering from the side where a bed of glass beads was situated). When reaction eqiulibrium had been established, the gases leaving the reactor were trapped and the products obtained were analysed by gas phase chromatography (products whose structure was confirmed by mass spectrometry).

The selectivity "CY" is defined as being the quantity in mole(s) of TFE substrate obtained relative to the quantity in mole(s) of 1-chloro-2,2,2-trifluoroethane converted.

The ratio "RR" corresponds to the ratio between the quantity of moles which were converted into desired product and the initial quantity of substrate during the reaction. "DC" corresponds to substrate.

TYPICAL TEST

The reactions were performed in a vapour phase reactor, tubular stationary bed having a length of 200 mm, and a diameter of 15mm and made of quartz.

Nitrogen and the flugen ($CF_3$—$CH_2Cl$) were introduced via volumetric flow meters which are sold under the trade name "Brooks" (the precise quantity of flugen introduced was determined by weighing the flugen bottle before and after reaction). Water was introduced with the aid of a syringe actuated by a syringe driver. The reactor was then placed in a shell oven equipped with a temperature controller.

Test sequence:

The catalyst was charged to the reactor and then a bed of glass beads was charged on the catalyst.

The reactor was heated to the reaction temperature in air until thermal equilibrium was established (1 hour). The reactant were injected over a period of 30 minutes. This conditioning treatment promoted good selectivity.

The amide reaction product was trapped for 1 hour in traps containing n-propanol and then analyses were made.

The following experimental conditions were used:

The temperature was 490° C. The flugen flow rate was 46 mmol/h (5.45 g/h). The H₂O flow rate was 230 mmol/h =4.14 g/h, and the N₂ flow rate was 1.05 l/h. The catalyst was LaPO₄, Cs (CsOH) which had been obtained during example No. C4.

3 ml of powder (4.4 g) was dispersed in 5 ml of quartz granules having a mean diameter 0.6 mm. The volume ratio of H₂O/F133 was 5 and the catalyst flow rate was 1.24 H⁻¹ Results:

Flugen 133 DC=22%
Trifluoroethanol RR=19.9%
Trifluoroethanol CY=90%

Preliminary tests on catalysts 1, 2, 3, 5 and 6 showed that all exhibited a catalytic activity. It was observed that the alkali metals were better than the alkaline-earth metals and that the selectivity increased with atomic number.

When the alkaline earth metal was strontium, the conversion yield was 19%, RR was 4% and selectivity was 21%. When barium was used, the conversion yield was 25%, RR was 3.3% and selectivity was 13%.

Example No. 1

57 g of $H_3PO_4$ (85%; d=1.7; PROLABO) and 150 ml of water were introduced into a 1-liter three-necked flask. Stirring was applied at 500-700 revolutions/minute. The mixture was heated to 90° C.

While stirring, 80.5 g of $La_2O_3$ (PROLABO) were added in over a period of 30 to 40 minutes (2 to 3 portions approximately every 4 to 5 minutes). The temperature was maintained between 87° C. and 93° C.

After the addition, stirring was stopped in order to rinse the inner surface with 50 to 70 grams of water. Stirring was continued 500-700 revolutions/minute for 1 hour and 15 minutes at An NaOH solution was prepared by diluting a mass of NaOH (PROLABO) (with the assumption the NaOH had no carbonate) in 25 ml of water for 125 mmoles of NaOH. While stirring at 500 to 700 revolutions/minute, the NaOH solution was added to the suspension. continuously for 20 to 30 seconds. The stirring was then stopped and the inner surface rinsed with 50 to 70 grams of water.

Stirring was continued at 500 to 700 revolutions/minute and heating occurred for 1 hour and 15 minutes at 90° C. The mixture was then allowed to cool to room temperature while being stirred for a half-hour. Cooling was finished in a bath of cold water. The resulting thick suspension was filtered on a No. 3 sinter (d=130) until the mother liquor was depleted.

The product remained moist. The sinter was washed with 250 ml water while stirred with a spatula (plastic or stainless steel); the suspension appeared homogeneous. The washing operation was repeated another two times.

At each stage, filtration occurred until the dilution waters had been depleted. 1,000-1,100 ml of mother liquor and dilution waters were recuperated. The minimum pH of the recuperated waters was 9.

The total duration of the synthesis was about one day. The cake that was left on the sinter was dried for one night at 100° C. in a void (60 mm Hg). The product obtained was ground easily and brought to the desired particle type. The solid was charred for 2 hours and 30 minutes at 500° C. in surrounding air and then left to cool in air at room temperature.

Example No. 2

The procedure of Example No. 1 was repeated except NaOH was replaced with KOH (PROLABO).

Example No. 3

The procedure of Example No. 1 was repeated except NaOH was replaced with CsOH.H₂O (PROLABO).

Example No. 4

The procedure of Example No. 1 was repeated except NaOH was replaced with LiOH (PROLABO).

Example No. 5

The procedure of Example No. 3 was repeated except for the neutralization and washing stage, which was as follows.

a) neutralization of the reaction mixture was carried out with a 6M solution of CsOH until the pH of the mother liquors reached a value of 9, which was after the addition of approximately 45 cc of basic solution;

b) the product obtained after filtering was not subjected to any washing. The product was then dried at 110° C. overnight and was calcined at 500° C. for 2 hours. The dry sample thus obtained contained 6% by weight of cesium.

Example No. 6 stage. Instead the product filtered off was then resuspended in demineralized water with stirring for half an hour at room temperature. The suspension was such that there was 30 ml of water per equivalent of wet product of 10 grams of product dried at 110° C.

The suspension was then centrifuged. The product was dried at 110° C. overnight and was calcined at 500° C. for 2 hours. The dry sample thus obtained contained 3% by weight of cesium.

Example No. 7

The procedure was the same as in Example No. 6, except the washing was repeated twice. The product was then washed three times and then dried at 110° C. overnight and calcined at 500° C. for 2 hours. The dry product thus obtained contained 1% by weight of cesium.

Example No. 8

57 g of $H_3PO_4$ (85%, Prolabo) and 150 ml of water were introduced into a 1-liter three-necked flask. Stirring was applied at 500-700 revolutions/minute. 166.6 g of $La_2(CO_3)_3.12H_2O$ were introduced cold, slowly and with energetic stirring.

The reaction mixture was then heated to 90° C. over a period of one hour, and then cooled to room temperature with stirring over period of half an hour. Cooling was finished in a cold water bath.

The suspension was filtered on a No. 3 sinter until the mother liquors were exhausted. The product was then redispersed in a liter of water with energetic stirring and left in suspension for half an hour while stirring was continued. The product was again filtered on a No. 3 sinter. This washing operation was repeated another two times.

The product was then filtered off and dried at 110° C. The product had a water pore volume of 0.4 cc/g and was used as the product which was impregnated, hereafter called "the product to be impregnated."

4.7 cc of a 6M solution of CsOH were measured, to which 14.12 cc of a 1M solution of $H_3PO_4$ were added. The quantity of water needed to make up to 50 cc was then added. 50 g of product to be impregnated were taken and placed in a 200 cc beaker. 20 cc of the impregnating solution were introduced dropwise while the agglomerates formed were crushed and good homogeneity was produced.

The product was left standing for 1 hour, then dried overnight at 110° C. and finally calcined at 500° C. for 2 hours. The product was hexagonal in structure, and the dry product contained 3% by weight cesium.

Example No. 9

The procedure of Example No. 8 was repeated except with a different impregnating solution prepared by making up to 50 cc a solution of 4.7 cc of 6M CsOH. The solution obtained was 0.564 molar.

50 g of the product to be impregnated were then impregnated with 20 cc of this solution by following the procedure shown in Example 8. The product was then dried at 110° C. overnight and calcined at 500° C. for 2 hours.

Example No. 10

50 g of product to be impregnated were impregnated with 20 cc of a 0.188 molar solution of $Cs_3LaCl_6$. The procedure of Example No. 8 was then followed.

Example No. 11

50 g of product to be impregnated were impregnated with 20 cc of a 0.564 molar solution of CsF. The procedure of Example No. 8 was then followed.

Example No. 12

50 g of the product to be impregnated were impregnated with 20 cc of a 0.282 molar solution of $Cs_2SO_4$. The procedure of

Example No. 13

The procedure of Example No. 8 was repeated with a 0.282 molar solution of $Cs_2CO_3$.

Example No. 14

The procedure of Example No. 8 was repeated with a 0.282 molar solution of $Cs_2C_2O_4$.

Example No. 15

The procedure Example No. 8 was repeated with a 0.564 molar solution of cesium benzoate.

Example No. 16

The procedure of Example No. 1 was repeated until the neutralisation with the strong inorganic base.

At this stage the product was filtered off on a No. 3 sinter the product was stirred with a spatula. The product was then dried overnight at 110° C.

The product was redispersed with stirring in a liter of distilled water. A 6N solution of CsOH was then added until the pH of the solution was 9, while energetic stirring was maintained at room temperature.

The product was then filtered off on a No. 3 sinter and washed three times on the sinter with 250 ml of distilled water. The product was dried at 110° C. overnight and calcined at 500° C. for

Example No. 17

0.75 l of a 0.5 molar solution of $La(NO_3)_3$ (A) and 0.5 liters of a 0.75 molar solution of $(NH_4)_2HPO_4$ (B) were prepared. Solutions A and B were then heated separately to 80° C. Solution B was added to solution A over half an hour with energetic stirring and the temperature was then raised to 90° C. This temperature was maintained for one hour, and then the temperature was allowed to drop to 80° C.

75 cc of a 6M solution of CsOH were then added to the reaction mixture. The mixture was cooled and the suspension was centrifuged. The product was then redispersed with stirring in 1000 of distilled and filtered water. 3 washings were carried out and the product was then dried at 110° C. The water pore volume of the product obtained was 1 cc/g.

50 cc of a solution of CsOH and $H_3PO_4$ were prepared from 3.76 cc of 3M CsOH and 5.64 cc of 1M H₃PO₄. The procedure of Example No. 8 was repeated, but with 10 cc of solution per 10 g of product.

Example No. 18

The product obtained in Example No. 8, which was dried at 110° C. overnight after impregnation, was calcined at 700° C. for 2 hours. This product was monoclinic in structure.

Example No. 19

The product to be impregnated obtained in Example 8, which was dried at 110° C. before impregnation, was calcined at 700° C. for 2 hours. The structure changed from the hexagonal phase to the monoclinic phase. The product had a pore volume of 0.28 cc/g.

A solution of 100 cc of CsOH and $H_3PO_4$ was prepared from 22.03 cc of 1.5M CsOH and 16.52 cc of 1M $H_3PO_4$. 10 g of the The product was then dried at 110° C. overnight and calcined at 500° C. for 2 hours.

Example No. 20

The synthesis of Example No. 1 was repeated with $La_2O_3$ replaced by $Sm_2O_3$ (mole for mole), until just before the neutralization stage. The product was then filtered off, washed on a sinter three times and dried at 110° C. overnight. The produce had a pore volume of 0.35 cc/g.

10 g of the product were then impregnated with 3.5 cc of the cc of a solution of CsOH and $H_3PO_4$, prepared from 5.16 cc of 3M. CsOH and 7.74 cc of 1M $H_3PO_4$ by following the procedure of Example

Example No. 21

The impregnation procedure of Example 8 was repeated on a solid type of calcium hydrogen phosphate of high purity ($CaHPO_4 \cdot nH_2O$) with a surface area of approximately 30 m²/g, and a product of the same specific surface area was obtained.

General Remarks

Rare-earth phosphates and rare-earth alkali metal phosphates can be prepared by:
(1) solid-solid reaction of a mechanical mixture of salts of derivative cations and of phosphate. The mixture is heated to a temperature above the highest melting temperature of the salts present. The reaction may be conducted in an open environment or in a closed environment in inert atmosphere or otherwise, according to whether there is any gas release or not; or
(2) coprecipitation in an aqueous, ammonia or organic medium of a mixture of the salts of derivative cations and of a source of phosphate. The reaction may be conducted at a temperature below 100° C. in a conventional open or closed reactor which may be purged with an inert gas. It may be also conducted at a temperature above 100° C. in an autoclave with or without stirring.

The order of addition of the cation salts and of the phosphate source is not critical. The cation salts may first of all be mixed in a solution and the phosphate source may be added, or vice versa. Precipitation commences as soon as the phosphate is added. It is also possible to precipitate the rare earth phosphate first, before adding the alkali metal salt to the reaction mixture. It is also possible to premix the alkali metal salt and the phosphate source and then to add the rare earth salt to this mixture.

The mixing of the cation salts and the precipitation by adding the phosphate source can be done cold or hot. If the precipitation is done cold, it may be followed by an aging period with heating, in an open reactor in the case of a temperature not exceeding 100° C., in an autoclave above this.

The precipitation reaction can be performed at any pH between a 0.5 and 13. It is preferably conducted between pH of 1 and 10 and more preferably between pH of 1 and 6.

The pH of the mixture is a function of the nature of the also be adjusted with an inorganic (HCl, $NO_3$) or organic acid or an inorganic (NaOH, CsOH, $NH_4OH$) or organic (amine, benzoic acid, oxalio acid, etc.) base to the desired value before or during precipitation.

The pH can also vary during precipitation:
either due to natural variation during the addition of one of the reactants to the other, the pH then changing from the basic region toward the acidic region or vice versa;
or by adding a so-called retarding base (urea, etc.) to the acidic reaction mixture. In this case, mixing of the cation salts, of the phosphate source and of the retarding base is carried out at a sufficiently low pH to prevent any precipitation. The reaction mixture is heated and the pH is raised by thermal decomposition of the retarding base, resulting in a homogeneous precipitation.

The precipitation reaction can optionally take place in the presence of an organic agent of quaternary ammonium type of
general formula $R_4N^+X^-$ where R is an alkyl containing at least one carbon and $X^-$ is a halide or a hydroxide.

The coprecipitation reaction can be performed with or without stirring, but preferably with stirring.

The products thus obtained can or need not be washed with an acidic, neutral or basic aqueous solution, the pH of the solution being controlled using an acid or a base which is inorganic (HCl, $NH_4OH$, NaOH) or organic (acetic acid, tetrapropylammonium hydroxide, etc.).

The washing can also be performed with an organic solvent, such as methanol, toluene and the like. The washing can also be performed by resuspending in water, or by filtering on a filter.

The product obtained after washing can or need not be dried at approximately 110° C. under normal atmosphere or under partial vacuum or by freeze-drying.

It can also be calcined up to 900° C., preferably not more than 500° C., for a period ranging from one hour to 10 hours.

The product thus obtained can also be chemically modified by impregnation by a dry or wet route. Dry impregnation consists of adding to a mass $m_1$ of a powder of the product to be impregnated to a volume V of an aqueous solution of one or more salts of cations or of anions to be fixed on the surface of the solid. The volume $V/m_1$ of solution is chosen such that V is equal to the water pore volume of the solid to be impregnated.

The cation or anion concentration C of the impregnating solution is chosen such that the ratio $$CVM_2/ml = \Omega$$

is equal to the chosen percentage by weight of impregnating species which is fixed on the surface of the product to be impregnated. $M_2$ = molecular mass of the impregnating species. The addition of the solution is carried out dropwise to obtain a homogeneous absorption.

The product can then be left at rest for a variable period at conventional methods which are known to a person skilled in the calcined at least 500° C. for 2 hours.

The wet-route impregnation is performed by redispersing the solid obtained by solid-solid reaction or coprecipitation in an aqueous solution of salts of cations and/or of anions to be fixed on the surface of the solid.

This solution has a concentration ranging from $10^{-3}$ to 10 M in the impregnating species. The pH of the solution can advantageously be adjusted above the isoelectric point of the product to be modified in order to fix preferably the cations. The temperature of the solution can be from the ambient to 100° C.

The dispersion is stirred vigorously for a variable period. The product is then filtered off and optionally washed using the techniques described above. The product is then dried as indicated above and calcined at at least 500° C. for 2 hours.

Example No. 22

5 g of solid prepared according to Example No. 1 were placed in a tubular reactor. The combination of reactor and catalyst was heated to 490° C. over ½ hour. The mixture of the gaseous reactants, that is water and 1-chloro-2,2,2-trifluorethane, was then circulated over the solid. The reactants were mixed with nitrogen in the molar ratio $H_2O/N_2/CH_3CH_2Cl=5/1/1$. The gas flow at the reaction temperature was 18 l/h. In the reactor part, the gases were trapped and analyzed by gas phase chromatography.

After a period of approximately ½ hour (which enabled the reaction equilibrium to be reached) the following performance was observed:
Conversion of 1-chloro-2,2,2-trifluoroethane: 18.6%
Selectivity for trifluoroethanol: 38%
Selectivity for 1-chloro-2,2-difluoroethylene: 10.4%

Example No. 23

The procedure for Example No. 22 was repeated using 5 g of solid prepared according to Example No. 2.

Conversion of 1-chloro-2,2,2-trifluoroethane: 26%
Selectivity for trifluoroethanol: 53%
Selectivity for 1-chlorodifluoroethylene: 13%

Example No. 24

Use of the material according to the procedure of Example No. 22, prepared according to Example No. 3, resulted in the following performance:
Conversion of 1-chloro-2,2,2-trifluoroethane: 26%
Selectively for trifluoroethanol: 90%
Selectivity for 1-chlorodifluoroethylene: 6.4%

Example No. 25

The procedure of Example No. 22 was repeated with the aid of the material prepared according to Example 4:
Conversion of 1-chloro-2,2,2-trifluoroethane: 6%
Selectivity for trifluoroethanol: 38%
Selectivity for 1-chlorodifluoroethylene: 37%

Example No. 26

The following were obtained according to Example No. 22 by using the solid prepared according to Example No. 5:
Conversion of 1-chloro-2,2,2-trifluoroethane: 26.8%
Selectivity for trifluoroethanol: 87.7%
Selectivity for 1-chlorodifluoroethylene: 7.5%, Example No. 27

The following were obtained according to Example No. 22 by using the solid prepared according to Example No. 6:
Conversion of 1-chloro-2,2,2-trifluoroethane: 20.6%
Selectivity for trifluoroethanol: 93%
Selectivity for 1-chlorodifluoroethylene: 7%

Example No. 28

The following were obtained according to Example No. 22 by using the solid prepared according to Example No. 7:
Conversion of 1-chloro-2,2,2-trifluoroethane: 8.5%
Selectivity for trifluoroethanol: 88.3%
Selectivity for 1-chlorodifluoroethylene: 11.7%

Example No. 29

The following were obtained according to Example No. 22 by using the solid prepared according to Example No. 8:
Conversion of 1-chloro-2,2,2-trifluoroethane: 23.7%
Selectivity for trifluoroethanol: 90.7%
Selectivity for 1-chlorodifluoroethylene: 9.3%

Example No. 30

5 g of solid prepared according to Example No. 8 were placed in a tubular reactor. The combination of reactor and catalyst was heated to 435° C. for ½ h. The mixture of the gaseous reactant, that is water and 1-chloro-2,2,2-trifluoroethane, was then circulated over the solid.

These reactants were mixed with nitrogen in the molar ratio of $H_2O/N_2/CF_3CH_2Cl=5/1/1$. The gas flow at the reaction temperature was 10 l/h. On leaving the reactor the gases were trapped and then analyzed by gas phase chromatography:
Conversion of 1-chloro-2,2,2-trifluoroethane: 10.6%
Selectivity for trifluoroethanol: 95%.

Example No. 31

5 g of solid prepared according to Example No. 8 were placed in a tubular reactor. The combination of reactor and catalyst was heated to 470° C. for 1/2 h. The mixture of the gaseous reactants, water and 1-chloro-2,2,2-trifluoroethane, was then circulated over the solid.

These reactants were mixed with nitrogen in the molar ratio of $H_2O/N_2/CF_3CH_2Cl=3/1/1$. The gas flow at the reaction temperature was 13 l/h. On leaving the reactor the gases were trapped and analyzed by gas phase chromatography:
Conversion of 1-chloro-2,2,2-trifluoroethane: 19.1%
Selectivity for trifluoroethanol: 93.2%
Selectivity for 1-chlorodifluoroethylene: 6.8%

Example No. 32

The following were obtained according to Example No. 22 by using the solid prepared according to Example No. 9:
Conversion of 1-chloro-2,2,2-trifluoroethane: 23%
Selectivity for trifluoroethanol: 87%
Selectivity for 1-chlorodifluoroethylene: 13%

Example No. 33

The following were obtained according to Example No. 22 by using the solid prepared according to Example No. 10:
Conversion of 1-chloro-2,2,2-trifluoroethane: 12%
Selectivity for trifluoroethanol: 60%
Selectivity for 1-chloro-2,2-difluoroethylene: 40%

Example No. 34

The following were obtained according to Example No. 22 by using the solid prepared according to Example No. 11:
Conversion of 1-chloro-2,2,2-trifluoroethane: 18.5%
Selectivity for trifluoroethanol: 82%
Selectivity for 1-chloro-2,2-difluoroethylene: 18%

Example No. 35

The following were obtained according to Example No. 22 by using the solid prepared according to Example No. 12:
Conversion of 1-chloro-2,2,2-trifluoroethane: 19.5%
Selectivity for trifluoroethanol: 89%
Selectivity for 1-chloro-2,2-difluoroethylene: 11%

Example No. 36

The following were obtained according to Example No. 22 by using the solid prepared according to Example No. 13:
Conversion of 1-chloro-2,2,2-trifluoroethane: 21%
Selectivity for trifluoroethanol: 81%
Selectivity for 1-chloro-2,2-difluoroethylene: 19%

Example No. 37

The following were obtained according to Example No. 22 by using the solid prepared according to Example No. 14:
Conversion of 1-chloro-2,2,2-trifluoroethane: 21.5%
Selectivity for trifluoroethanol: 66%
Selectivity for 1-chloro-2,2-difluoroethylene: 15%

Example No. 38

The following were obtained according to Example No. 22 by using the solid prepared according to Example No. 15:
Conversion of 1-chloro-2,2,2-trifluoroethane: 21%
Selectivity for trifluoroethanol: 80%
Selectivity for 1-chloro-2,2-difluoroethylene: 20%

Example No. 39

The following were obtained according to Example No. 22 by using the solid prepared according to Example No. 16:
Conversion of 1-chloro-2,2,2-trifluoroethane: 26%
Selectivity for trifluoroethanol: 68%
Selectivity for 1-chloro-2,2-difluoroethylene: 10%

Example No. 40

The following were obtained according to Example No. 22 by using the solid prepared according to Example No. 17:
Conversion of 1-chloro-2,2,2-trifluoroethane: 16.4%
Selectivity for trifluoroethanol: 86.5%
Selectivity for 1-chloro-2,2-difluoroethylene: 11.2%

Example No. 41

The following were obtained according to Example No. 22 by using the solid prepared according to Example No. 18:
Conversion of 1-chloro-2,2,2-trifluoroethane: 24.1%
Selectivity for trifluoroethanol: 91.7%
Selectivity for 1-chloro-2,2-difluoroethylene: 8.3%

Example No. 42

The following were obtained according to Example No. 22 by using the solid prepared according to Example No. 19:
Conversion of 1-chloro-2,2,2-trifluoroethane: 9%
Selectivity for trifluoroethanol: 39%
Selectivity for 1-chloro-2,2-difluoroethylene: 19%

Example No. 43

The following were obtained according to Example No. 22 by using the solid prepared according to Example No. 20:
Conversion of 1-chloro-2,2,2-trifluoroethane: 4%
Selectivity for trifluoroethanol: 95%

Example No. 44

The following were obtained according to Example No. 22 by using the solid prepared according to Example No. 21:
Conversion of 1-chloro-2,2,2-trifluoroethane: 14%
Selectivity for trifluoroethanol: 31%
Selectivity for 1-chloro-2,2-difluoroethylene: 16.4%

Example No. 45

5 g of solid prepared according to Example No. 1 were placed in a tubular reactor. The combination of reactor and catalyst was heated to 490° C. for ½ hour. The mixture of the gaseous reactants, water and 1-bromo-2,2,2-trifluoroethane, was circulated over the solid. These reactants were mixed with nitrogen in the molar ratio of $H_2O/N_2/CF_3CHJ_2Br = 5/1/1$. The gas flow at the reaction temperature was 18 l/h. On leaving the reactor the gases were trapped and then analyzed by gas phase chromatography.

After a period of one hour, which allowed the reaction equilibrium to be reached, the following performance was observed:
Conversion of 1-bromo-2,2,2-trifluoroethane: 5.6%
Selectivity for trifluoroethanol: 83.9%
Selectivity for 1-bromo-2,2-difluoroethylene: 16.1%

Example No. 46

The following were obtained according to Example No. 45 by using the solid prepared according to Example No. 2:
Conversion of 1-bromo-2,2,2-trifluoroethane: 17.4%
Selectivity for trifluoroethanol: 94.8%
Selectivity for 1-bromo-2,2-difluoroethylene: 5.2%

Example No. 47

The following were obtained according to Example No. 45 by using the solid prepared according to Example No. 3:
Conversion of 1-bromo-2,2,2-trifluoroethane: 23.4%
Selectivity for trifluoroethanol: 95.7%
Selectivity for 1-bromo-2,2-difluoroethylene: 4.3%

Example No. 48

5 g of solid prepared according to Example No. 3 were placed in a tubular reactor. The combination of reactor and catalyst was heated to 490° C. for ½ hour. The mixture of the gaseous reactants, water and 1,2,2,2-tetrafluoroethane, was then circulated over the solid. These reactants were mixed with flow at the reaction temperature was 18 l/h. On leaving the reactor the gases were trapped and then analyzed by gas phase chromatography.

After a period of one hour, which allowed the reaction equilibrium to be reached, the following performance was observed:
Conversion of 1,2,2,2-tetrafluoroethane: 11%
Selectivity for trifluoroethanol: >95%

Example No. 49

The following were obtained according to Example No. 48 by using the solid prepared according to Example No. 2:
Conversion of 1,2,2,2-tetrafluoroethane: 8.5%
Selectivity for trifluoroethanol: >95%

Example No. 50

The following were obtained according to Example No. 48 by using the solid prepared according to Example No. 1:
Conversion of 1,2,2,2-tetrafluoroethane: 5%
Selectivity for trifluoroethanol: >95%

Example No. 51

5 grams of a solid prepared according to Example 8 were placed in a tubular reactor. The reactor and catalyzer assembly was heated at 490° C. for a half-hour. The mixture of gaseous reactants, ammonia and chloro-1 trifluoro-2,2,2 ethane, was then circulated on the solid. These were mixed with nitrogen in a molar relation of $NH_3/N_2/CF_3CH_2Cl = 5/1/1$. The gaseous flux at the reaction temperature was 19 l/h. The gases were trapped at the exit of the reactor and analyzed chromatographically in the gaseous phase. The formation of a product was observed of which the retention time was identical to that of trifluoroethylamine.

What is claimed is:

1. A chemical compound which, when dry, corresponds to formula (I):

$$(EO_4M).(Imp)_p \qquad (I)$$

wherein
E is selected from phosphorus, arsenic, antimony and bismuth;
M is a metal or a mixture of metals such that:

$$M = \alpha M_1^+ + \beta M_2^{++} + \gamma M_3^{3+} + \delta M_4^{4+}$$

with the relationship $\alpha = 2\beta + 3\gamma + 4\delta = 3$;
wherein $M_1$ is selected from lithium, sodium, potassium, rubidium, cesium, francium and mixtures thereof;
$M_2$ is selected from divalent transition elements, alkaline earth metals and mixtures thereof;
$M_3$ is selected from trivalent transition elements, boron, aluminum, gallium, indium, thallium, the elements having an electron sub-shell f, and mixtures thereof;
$M_4$ is selected from tetravalent rare earths, titanium, hafnium, tin, germanium and silicon;
$\alpha$ is a coefficient between 0 and 3;
$\beta$ is a coefficient between 0 and 3/2;
$\gamma$ is a coefficient between 0 and 1;
$\delta$ is a coefficient between 0 and 3/4;
Imp is different from $EO_4M$ and corresponds to a basic impregnating compound selected from alkaline earth metals, alkali metals and mixtures thereof combined with a counter-anion to ensure electrical neutrality;
the coefficient p is between $10^{-2}$ and ⅓; and $\alpha + p$ is less than or equal to 3.3 and greater than or equal to $10^{-2}$.

2. The chemical compound as claimed in claim 1, wherein E is phosphorus.

3. The chemical compound as claimed in claim 1, wherein the coefficient p is between $½ \times 10^{-1}$ and ¼.

4. The chemical compound as claimed in claim 1, wherein $\alpha$ is a coefficient from greater than 0.01 to 3.

5. The chemical compound as claimed in claim 1, wherein $\beta$ is a coefficient between 0 and ⅓.

6. The chemical compound as claimed in claim 1, wherein $\gamma$ is a coefficient between ⅓ and 1.

7. The chemical compound as claimed in claim 1, wherein $\delta$ is a coefficient between 0 and ¼.

8. The chemical compound as claimed in claim 1, wherein $\alpha + p$ is between 0.05 and 1.

9. The chemical compound as claimed in claim 8, wherein $\alpha + p$ is between 0.05 and ½.

10. The chemical compound as claimed in claim 1, wherein $M_2$ is selected from calcium, strontium, barium, and mixtures thereof.

11. The chemical compound as claimed in claim 1, wherein $M_3$ is selected from metals having an electron sub-shell f, and mixtures thereof.

12. The chemical compound as claimed in claim 1 wherein $M_1$ is selected from potassium, sodium, rubidium, cesium and mixtures thereof.

13. The chemical compound as claimed in claim 1 wherein $M_1$ is selected cesium.

14. The chemical compound as claimed in claim 11, wherein said metal $M_3$ is selected from yttrium, rare earths, and mixtures thereof.

15. The chemical compound as claimed in claim 14, wherein said rare earths are selected from lanthanum and lanthanides.

16. The chemical compound as claimed in claim 1, wherein the mixtures thereof.

17. The chemical compound as claimed in claim 16, wherein the alkali metal is cesium.

18. The chemical compound as claimed in claim 1, wherein said counter-anion is selected from an $OH^-$ ion, or a mixture containing $OH^-$ ion.

19. A catalyst for the solvolysis or dehydrohalogenation of a halogenated compound, which comprises at least partially of a chemical compound which, when dry, corresponds to formula (I):

$$(EO_4M).(Imp)_p \qquad (I)$$

wherein
E is selected from phosphorus, arsenic, antimony and bismuth;
M is a metal or a mixture of metals such that:

$$M = \alpha M_1^+ + \beta M_2^{++} + \gamma M_3^{3+} + \delta M_4^{4+}$$

with the relationship $\alpha = 2\beta + 3\gamma + 4\delta = 3$;

wherein $M_1$ is selected from lithium, sodium, potassium, rubidium, cesium, francium and mixtures thereof;

$M_2$ is selected from divalent transition elements, alkaline earth metals and mixtures thereof;

$M_3$ is selected from trivalent transition elements, boron, aluminum, gallium, indium, thallium, the elements having an electron sub-shell f, and mixtures thereof;

$M_4$ is selected from tetravalent rare earths, titanium, hafnium, tin, germanium and silicon;

$\alpha$ is a coefficient between 0 and 3;

$\beta$ is a coefficient between 0 and 3/2;

$\gamma$ is a coefficient between 0 and 1;

$\delta$ is a coefficient between 0 and $\delta$;

Imp may be the same as or different from $EO_4M$ and corresponds to a basic impregnating compound selected from alkaline earth metals, alkali metals and mixtures thereof combined with a counteranion to ensure electrical neutrality;

the coefficient p is between $10^{-2}$ and $\frac{1}{3}$;

and $\alpha + p$ is less than or equal to 3.3 and greater than or equal to $10^{-2}$.

20. The catalyst as claimed in claim 19, wherein said compound (I) is predominantly at the surface of said catalyst.

21. The catalyst as claimed in claim 20, wherein the remainder of said catalyst is produced from compounds selected from phosphates, hydrogen phosphates and compounds of the formula (II).

$EO_4M$.

22. The catalyst as claimed in claim 19, wherein the catalyst consists entirely of said compound (I).

23. A process for the production of a catalyst as claimed in claim 19, which comprises the steps of:
a) synthesizing a compound of formula (II), $EO_4M$; then;
b) introducing an impregnating compound Imp as defined in claim 19 into the reaction mixture;
c) separating any residual liquid from the reaction solid; and
d) drying and calcining the solid at a temperature greater than 100° C. to obtain the catalyst as claimed in claim 19.

24. A process for the synthesis of a compound as claimed in claim 1 which comprises the step of carrying out said synthesis of the compound in the presence of an alkali metal and a counteranion ensuring electrical neutrality.

25. The chemical compound as claimed in claim 1, wherein $\alpha$ is a coefficient from greater than 0.01 to 0.5.

26. The chemical compound as claimed in claim 1, wherein $\alpha$ is a coefficient between 0.05 and 0.2.

27. The chemical compound as claimed in claim 1, wherein the alkali metal is lithium.

* * * * *

UNITED STATES PATENT AND TRADEMARK OFFICE
CERTIFICATE OF CORRECTION

PATENT NO. : 5,118,651

DATED : June 02, 1992

INVENTOR(S) : Michel Gubelmann et al.

It is certified that error appears in the above-identified patent and that said Letters Patent is hereby corrected as shown below:

Title Page, Assignee, change "Cedex" to --Courbevoie Cedex--.

Claim 1, column 17, line 59, change "=" (first occurence) to --+--.

Claim 16, column 18, line 49, after "wherein the" insert --alkali metal is selected from potassium, rubidium, cesium, and --.

Claim 19, column 19, line 1, change "=" (first occurence) to --+--.

Claim 19, column 19, line 16, after "and" change " $\delta$ " to -- $\frac{2}{3}$ --.

UNITED STATES PATENT AND TRADEMARK OFFICE
CERTIFICATE OF CORRECTION

PATENT NO. : 5,118,651

DATED : June 2, 1992

INVENTOR(S) : Michel Gubelmann et al.

It is certified that error appears in the above-indentified patent and that said Letters Patent is hereby corrected as shown below:

Claim 21, column 20, line 2, change "(II)." to --(II):--.

Signed and Sealed this

Second Day of November, 1993

Attest:

BRUCE LEHMAN

Attesting Officer

Commissioner of Patents and Trademarks